US006668190B2

(12) United States Patent
Iezzi et al.

(10) Patent No.: US 6,668,190 B2
(45) Date of Patent: Dec. 23, 2003

(54) METHOD AND APPARATUS FOR ACTIVATING MOLECULES TO STIMULATE NEUROLOGICAL TISSUE

(75) Inventors: Raymond Iezzi, Troy, MI (US); Greg Auner, Livonia, MI (US); Patrick McAllister, Woodhaven, MI (US); Gary W. Abrams, Ann Arbor, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 09/881,549

(22) Filed: Jun. 14, 2001

(65) Prior Publication Data

US 2002/0042638 A1 Apr. 11, 2002

Related U.S. Application Data

(60) Provisional application No. 60/212,214, filed on Jun. 16, 2000.

(51) Int. Cl.[7] ................................................. A61N 1/30
(52) U.S. Cl. ...................... 604/20; 422/82.11; 422/99
(58) Field of Search .............................. 607/88, 53, 54; 604/19–20; 422/99–100, 82.11

(56) References Cited

U.S. PATENT DOCUMENTS

| 3,900,034 A | | 8/1975 | Katz et al. ................... 128/395 |
| 5,445,608 A | * | 8/1995 | Chen et al. .................... 604/19 |
| 5,474,528 A | * | 12/1995 | Meserol ........................ 604/20 |
| 5,505,726 A | | 4/1996 | Meserol .......................... 606/9 |
| 5,586,982 A | * | 12/1996 | Abela ............................ 604/20 |
| 5,935,155 A | | 8/1999 | Humayun et al. ............. 607/54 |
| 6,099,864 A | * | 8/2000 | Morrison et al. ............. 264/4.1 |
| 6,159,196 A | * | 12/2000 | Ruiz ............................ 604/46 |
| 6,242,258 B1 | * | 6/2001 | Haselton et al. ............. 514/396 |
| 6,310,083 B1 | * | 10/2001 | Kao et al. .................... 514/396 |
| 6,395,232 B1 | * | 5/2002 | McBride ...................... 422/100 |

FOREIGN PATENT DOCUMENTS

| EP | 0820786 | 1/1998 | ............ A61N/5/06 |
| WO | WO-01/49346 | 7/2001 | ............ A61M/5/00 |

* cited by examiner

*Primary Examiner*—Linda C. M. Dvorak
*Assistant Examiner*—Henry M. Johnson
(74) *Attorney, Agent, or Firm*—Schwegman, Lundberg, Woessner & Kluth, P.A.

(57) ABSTRACT

A drug delivery system includes a plurality of sites, a fluid channel for delivering a drug to one of the plurality sites, and a light channel for delivering light to an area near one of the plurality of sites. The fluid channel is a micro fluidic channel and the light channel is a wave guide. The light channel may also be a fiber optic cable. The light channel directs light at the fluid channel wherein light from the light channel does not substantially exit to the major surface. The drug delivery system selectively delivers drugs to various types of neurologic cells. In operation a solution of a photoactivatable neuro-active drug is delivered to a preselected area in vivo and photoactivated in the solution at the preselected area to stimulate neurological tissue. The neuro-active drug could be an antagonist or agonist of neuronal activity.

37 Claims, 11 Drawing Sheets

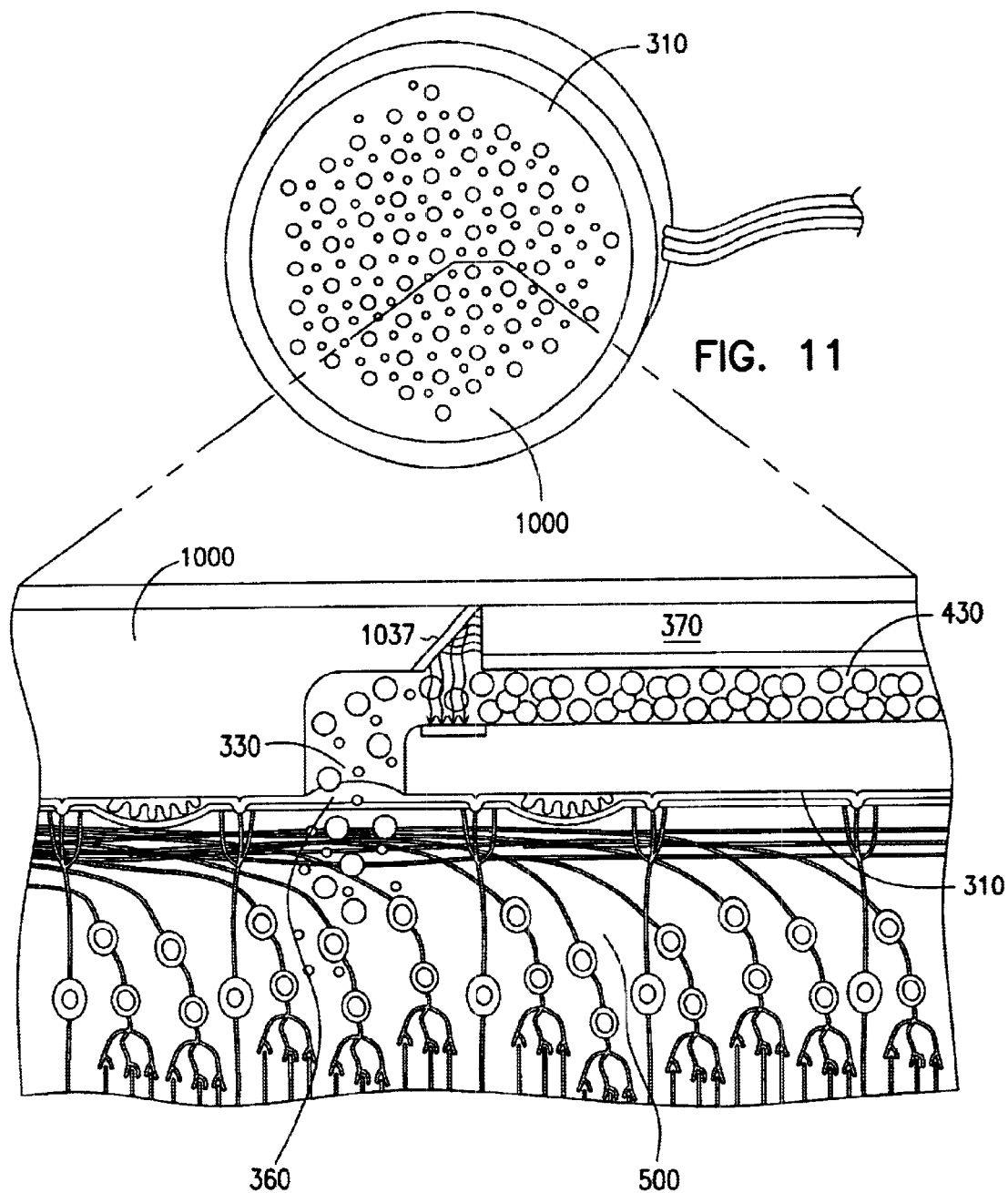

METHOD AND APPARATUS FOR ACTIVATING MOLECULES TO STIMULATE NEUROLOGICAL TISSUE

RELATED APPLICATION

This application claims the benefit of U.S. Provisional Application Ser. No. 60/212,214 filed Jun. 16, 2000 under 35 U.S.C. 119(e).

FIELD OF THE INVENTION

The present invention relates to the field of drug delivery. More particularly, this invention relates to a method of stimulating neurological tissue as part of a prosthetic device.

BACKGROUND OF THE INVENTION

There are several types of prosthetic devices used for stimulation of neural tissue or neurons. There are visual prostheses used to artificially restore vision in blind patients, which are currently being developed, and auditory prostheses used to artificially restore hearing. Currently, the method used to stimulate neural tissue associated with the visual and auditory systems includes developing devices and software for the application of electrical current to neural tissue. The basis of this technology was established in the late 1960s by Brindley who implanted arrays of surface stimulation electrodes in human visual cortical to generate the perception of multiple light flashes. These perceptions, called phophenes, can be arranged in a spatially organized manner so as to produce a primitive form of patterned vision. All implants under current development in these laboratories are designed to convert an electrical image into a patterned series of electrical impulses that, through a specially designed electrode array, will deliver current to the neural tissue to produce a visual perception. Currently, a cortical implant, which involves the placement of an electrode array in contact with the visual cortex, is being developed by a number of groups, worldwide. In addition, a retinal implant, which involves an electrode array placed either in front of (epiretinal) or beneath (sub-retinal) the retinal tissue is also being developed by a number of groups, worldwide. These electrode arrays are designed to deliver electrical impulses to stimulate currents to the retina in a spatially organized manner so as to produce visual perceptions through phophenes.

Electrode arrays have certain problems that lead to technical difficulties. Among the technical difficulties are that electrode arrays are not necessarily biocompatible. Electrode arrays are comprised of metal and often present the complication of oxidation at their termini. Electrode breakdown may result when metal atoms are deposited in tissues as the result of electrical current passage through electrodes placed in conducting body-fluid media. This may result in tissue toxicity as well as functional degradation of electrode performance. Increased electrical current may then become necessary to elicit the perception of phosphenes. This can lead to further tissue toxicity as a result of increased heat production at the electrode/tissue interface. In addition, from a physiological standpoint, electrical current lacks specificity with regard to the cell types it stimulates.

Formed vision requires the appropriate stimulation of ON and OFF channels of the visual system. These channels are established within the retina, very early in the process of visual perception to define the borders of objects. When light strikes a photoreceptor, chemical signals are transmitted to ON-bipolar and OFF-bipolar cells. ON-bipolar cells increase the release of chemical neurotransmitters when their corresponding photoreceptors receive a light stimulus and decrease this release when light is withdrawn. OFF-bipolar cells decrease the release of chemical neurotransmitters when their corresponding photoreceptors receive a light stimulus and increase the release of chemical neurotransmitter when light is absent or withdrawn. These ON and OFF bipolar cells communicate with ON and OFF retinal ganglion cells. The retinal ganglion cells are the output cells of the retina, which act through neurotransmitter synapses. In this way, the retina establishes the edges of objects through chemically encoded messages by measuring the contrast between adjacent points within the visual world. Thus, when stimulating the retina for the purpose of prosthetic vision in patients who have lost their photoreceptors, both ON-center and OFF-center bipolar and ganglion cells must be stimulated in an appropriate manner, according to local regions of bright and dark within the visual scene.

The visual prostheses used to artificially restore vision in blind patients which are currently being developed use electrical current to stimulate the ON-center and OFF-center bipolar and ganglion cells. Electrical current, however is non-specific regarding the cell types stimulated. Thus, both ON-center and OFF-center cells are stimulated, simultaneously. This results in a loss of edge information. Consequently, the patient perceives an often amorphous bright or dark spot or banana shaped area of light called a phosphene. Current technology has demonstrated that the objects or shapes perceived by experimental test subjects often do not correlate with the intended stimulus pattern.

The perception is often not consistent with the spatial organization on the electrode array. The axon belonging to a cell is typically remote from the cell body (soma) or dendrites. The soma and dendritic portions of the cell represent the inputs of a neuron, while the axon is a signaling output structure. Electrical stimulation stimulates the retinal axons, such as the nerve fiber layer or the retinal ganglion cell axon, in addition to the dendrites and soma. The result is that the spatial organization of the electrode will not be spatially transferred to the cells. The electrode array is used to form pixels for stimulating the cells; however, when this is done, the spatial relation of the pixels will not be transferred directly to the cells that need stimulation for the prosthesis. The pixels will be displaced since the axons are typically remotely located from the center of the cell. In other words, a stimulation a single axon, or an axon bundle, will result in an unpredictable perception that is not spatially related to the intended site of stimulation.

What is needed is a method and apparatus for stimulation of cells. What is also needed is a method and apparatus that can be used to precisely stimulate certain cells. What is also needed is method for stimulating neural tissue to produce a predictable perception when spatial relation is needed. What is further needed is an implantable device that is biocompatible and that will remain biocompatible.

SUMMARY OF THE INVENTION

A drug delivery system includes a plurality of sites, a fluid channel for delivering a drug to one of the plurality sites, and a light channel for delivering light to an area near one of the plurality of sites. The fluid channel is a micro fluidic channel and the light channel is a wave-guide. The light channel may also be a fiber optic cable. At least a portion of the drug delivery system is housed on a chip. In the chip the light channel intersects the fluid channel. The chip further includes a major surface, and a minor surface. The plurality of sites are on the major surface. The fluid channel is adapted to deliver fluid to a site on the major surface. The light channel directs light at the fluid channel wherein light from the light channel does not substantially exit to the major surface. The drug delivery system also includes a light source operatively connected to the light channel and a pump in fluid communication with the fluid channel.

In one embodiment, the drug delivery system includes a digital light processor, which receives an input. The digital light processor outputs light in response to the input. In other embodiments, the drug delivery system includes electrodes positioned near a site. The drug delivery system selectively delivers drugs to various types of neurologic cells including those associated with the eyes, the ears, and spine as well as basal ganglion, and hypothalamus.

In operation a solution of a photoactivatable caged neuro-active pro-drug is delivered to a preselected area in-vivo and photolytically activated in the solution at the preselected area. The neuro-active pro-drug could be an antagonist or agonist of neuronal activity. More than one photolytically activated molecule could be placed in the solution.

Advantageously, the method and apparatus stimulates cells at the cell center (soma or dendrites) to precisely stimulate certain cells. This method and apparatus stimulates the neural tissue and produces a predictable perception when spatial relation is needed. A further advantage is that the resulting implantable device is biocompatible and remains biocompatible.

BRIEF DESCRIPTION OF THE DRAWINGS

FIG. 11 is a view of the major surface of another embodiment of a chip, which is a contoured implant, associated with the drug delivery system.

FIG. 12 is a cross section of a portion of the chip shown in FIG. 11.

DESCRIPTION OF THE PREFERRED EMBODIMENT

In the following detailed description of the preferred embodiments, reference is made to the accompanying drawings, which form a part hereof, and in which are shown by way of illustration specific embodiments in which the invention may be practiced. It is to be understood that other embodiments may be utilized and structural changes may be made without departing from the scope of the present invention.

Figure 1:
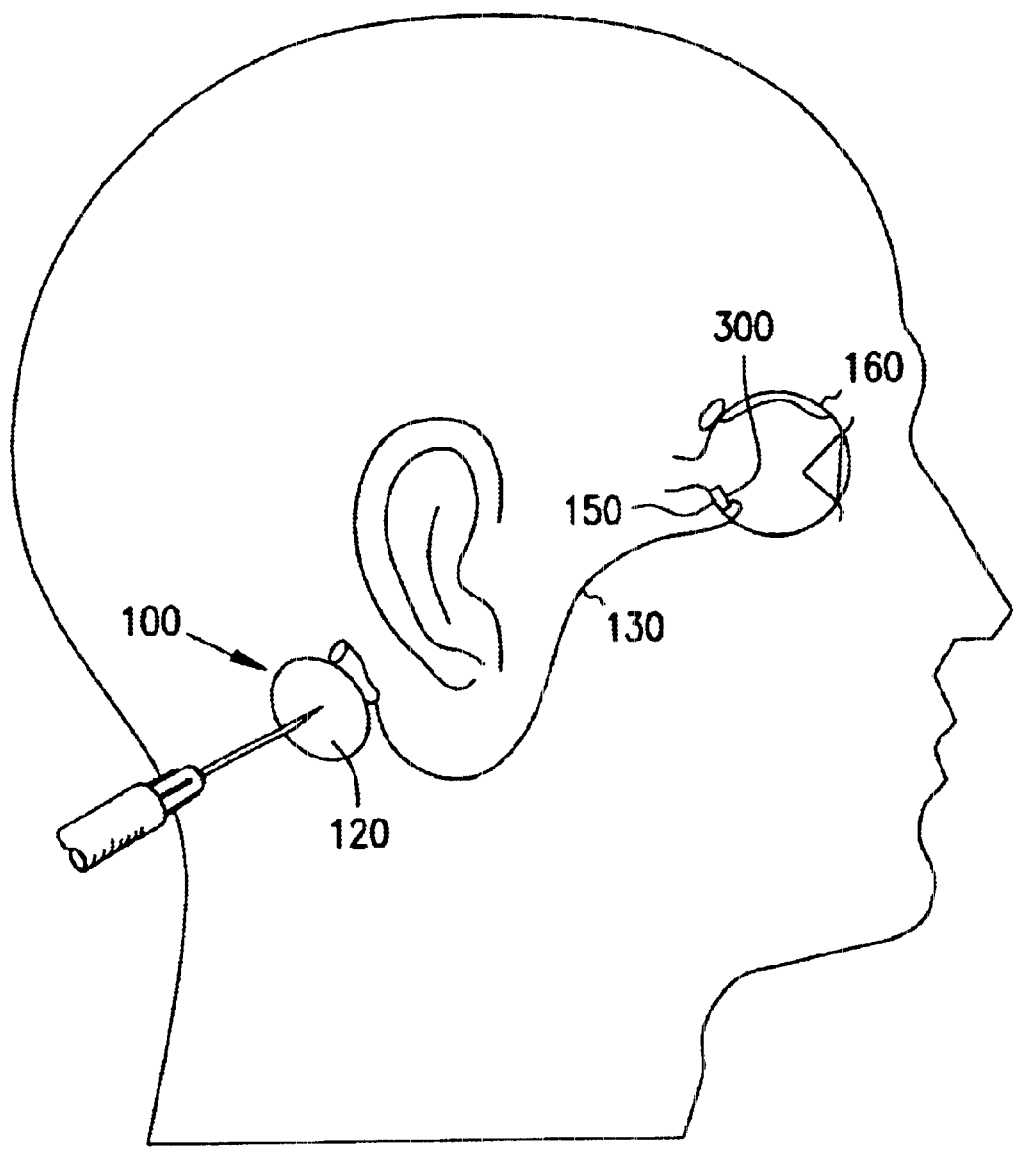
FIG. 1 is a schematic view of an implanted drug delivery device per this invention.

FIG. 1 is a schematic view of an implanted portion of a drug delivery device 100 per this invention. The implanted portion includes a pump 120 and a chip 300, which is in fluid communication with the pump 120. A tube 130 is connected between the pump 120 and the chip 300. The chip 300 is placed in contact with neurologic or non-neurologic tissue. As shown in FIG. 1, the neurologic tissue is associated with the retina 150 of the eye 160.

Figure 2:
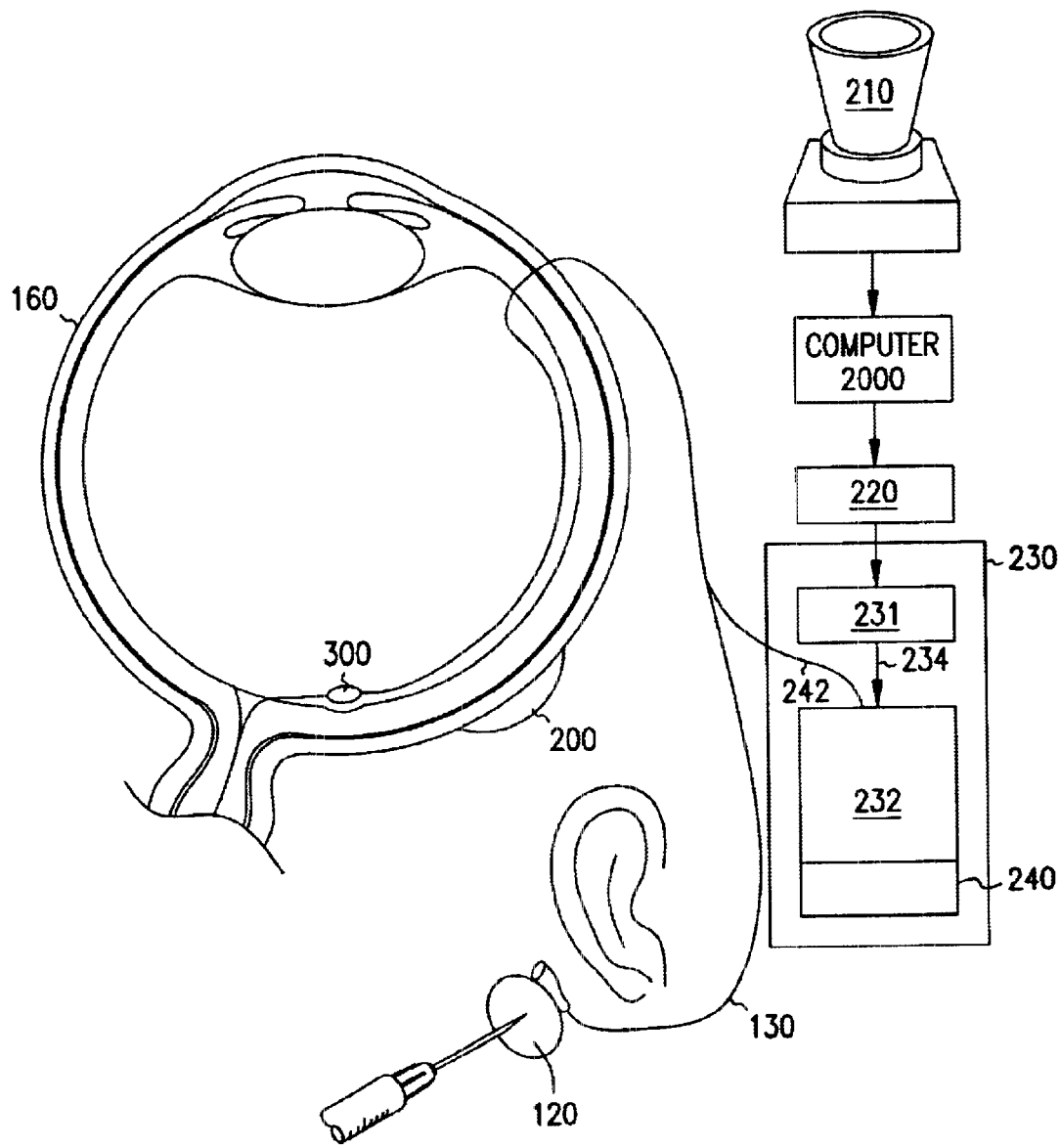
FIG. 2 is a schematic representation further detailing the drug delivery device.

FIG. 2 shows a schematic representation, which further details the drug delivery device 100. The drug delivery device includes the reservoir and pump 120, which includes a caged molecule used to stimulate neurologic tissue. The fluid reservoir is actually a solution, which includes the caged molecules, which can be activated by directing light of a certain wavelength to the caged molecules. In other words, the caged molecules contain a neuro-active pro-drug that is inactive until photo-activated. It should be noted that there may be one particular caged molecule within a solution, or there may be several different caged molecules that are photoactivatable within the solution. The solution may also contain active drugs that do not require uncaging. The tube 130 carries the caged molecules of the solution containing the caged molecules to a chip 300 which can also be termed as a wave-guide device that includes microfluidics. The solution is continually provided to the chip 300 so that the chip is essentially bathed in the solution associated with the drug delivery system 100. The chip includes a plurality of outlets for the solution that will be further detailed in the figures that follow. The chip 300 is in contact with neurologic tissues such as the retina of the eye. The solution from the chip is drained by a seton drainage implant 200.

In operation, a pump 120 moves a solution including caged molecules which can be photo activated from a reservoir to a chip 300 which is engaged or placed near neurologic tissue, such as neurologic tissue associated with the retina 150 of an eye 160. The solution is moved from the reservoir to the chip 300 where it bathes a major surface 310. After bathing the major surface 310 of the chip 300 the solution or fluid flows to a seton drainage implant 200 where it is removed from the area of interest. In the case of a visual implant, the drug delivery device 100 also includes a camera 210 and a computer 2000. The computer 2000 outputs a patterned light source that is then passed on to a first portion 231 of a link 230. The first portion 231 of the link 230 communicates with a second portion 232 of the link 230. There are several ways that the portions 231 and 232 of the link 230 can communicate with one another. This is represented by element 234 in the link 230. For example, the first portion 231 could directly link with the second portion 232.

In other words, the first portion of the link 231 may plug into the second portion of the link 232. In this case a patterned light source would be output to a first portion 231 along a series of fiber optic cables, and then to a connecter associated with the first portion 231 of the link 230. In a body there may be a trans-cutaneous optical link that represents the second portion 232 of the link 230. A trans-cutaneous link is one that crosses the skin or other tissue and would place the second portion 232 of the link 230 on or near the surface of the skin. Using a trans-cutaneous link, the first portion 231 of the link could directly optically couple to the second portion 232 of the link 230.

In another embodiment, the second portion 232 of the link 230 could be implanted within a body. The first portion 231 could produce a signal that could cross into the body, such as an RF or radio frequency signal. In other words, an RF signal could be used to pass optical or the patterned light source 220 between the first portion 231 and the second portion 232 of the link 230. The RF signal could be used to pass digital information derived from the computer-processed image of an electronic camera through the skin in an encoded manner. This digital information may then be decoded, interpreted and transformed into a patterned optical signal to be generated within the body by and implanted light source.

It should be noted that there are many forms of optical links or trans-cutaneous links where there would be a direct link between a first portion 231 of a link 230 and the second portion 232 of the link 230. In other words, the link may be an infrared link may use direct fiber connection or may be any other type of connection where link 231 would have to directly link-to-link portion 232.

The second portion 232 of the link 230 includes a light source 240. The light source 240 is connected to the microchip that includes wave-guides and microfluidic channels. A fiber optic cable or series of fiber optic cables connect the light source 240 to the chip 300. The light source generally will include a series of gallium nitride light emitting diodes that can be selectively turned on and off to send a portion of light down the fiber optic cable or bundle of cables 242 to the chip 300. The light is of a specific wavelength.

Figure 3:
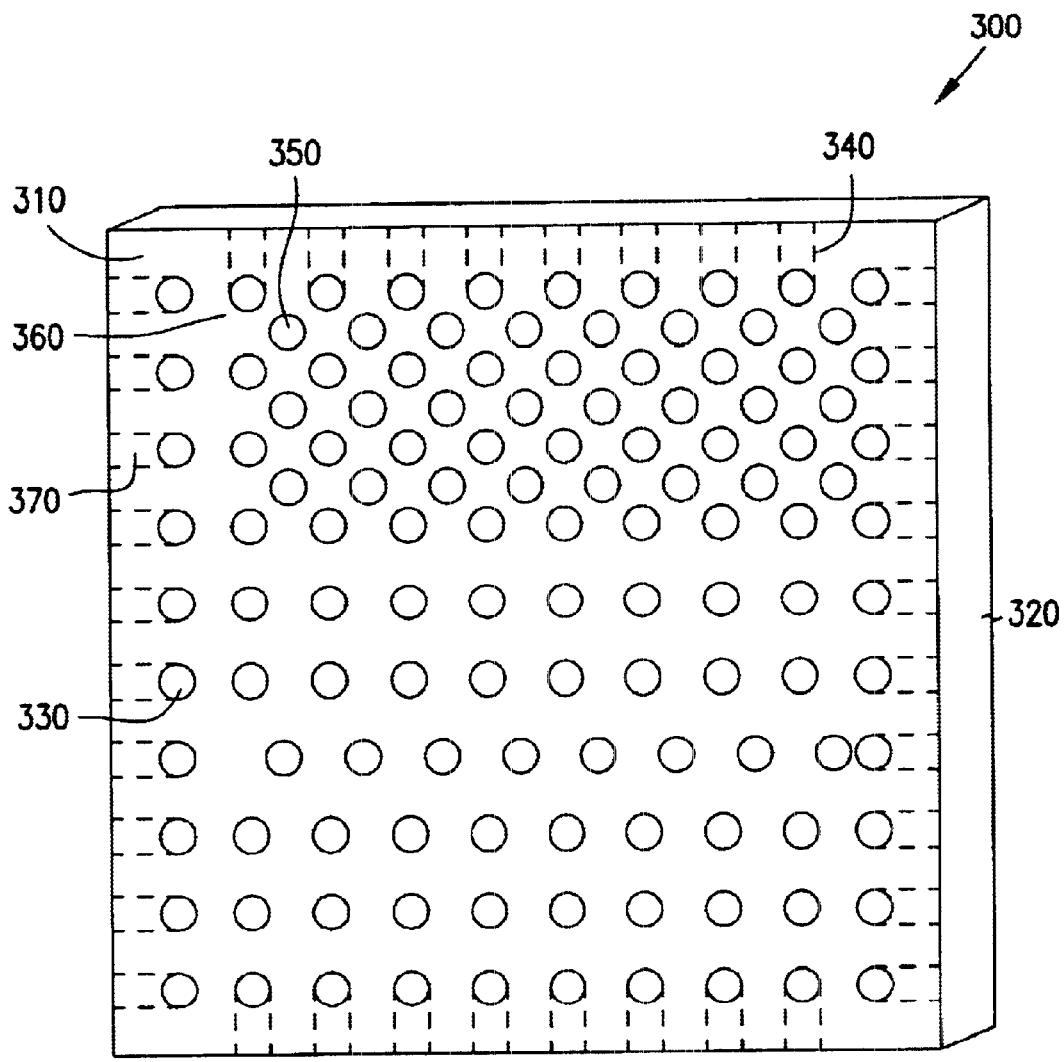
FIG. 3 is an isometric view of a chip including waveguides and microfluidic channels, which is a contoured implant which is part of the drug delivery device.

FIG. 3 is an isometric view of the chip 300 that includes a first major surface 310, a second major surface 310' and a minor surface 320. The chip 300 also includes a plurality of microfluidic channels or conduit that terminate at the major surface 310. The first major surface 310, when placed, is in contact or proximate the cells to be stimulated. The first major surface 310 includes elements for stimulating cells in contact or proximate to the first major surface 310. The second major surface 310' is devoid of the elements. The conduits are shown as circles and carry the reference numeral 330 in FIG. 3. The circles 330 can also be thought of as the ends of the conduits or the ends of the microfluidic channels within the chip 300. The chip 300 also includes a plurality of wave-guides that are represented by reference numeral 340 in FIG. 3. The chip 300 includes a plurality of dimples 350 on major surface 310 which are associated with a site where a portion of the solution including caged molecule will be delivered. The dimples 350 hold a set amount of the solution exiting the conduit ends 330. Each of the dimples 350 also can represent a site 360 on the chip 300. As can be seen, the dimples 350, and the conduit ends 330 each terminate at a site 360. The site 360 are in a grid. Each portion of the grid includes a dimple 350, a conduit end 330 for a fluid conduit, and a wave-guide 370. The dimple is a slight depression in the surface of the chip 300 which allows fluid from the fluid conduit 320 to puddle at the site 360 on the surface of the chip 300. The dimples 350 are optional. In addition, it should be noted that the chip need not be rectangular as shown. The chip 300 could be of any desired shape including circular.

Figure 4:
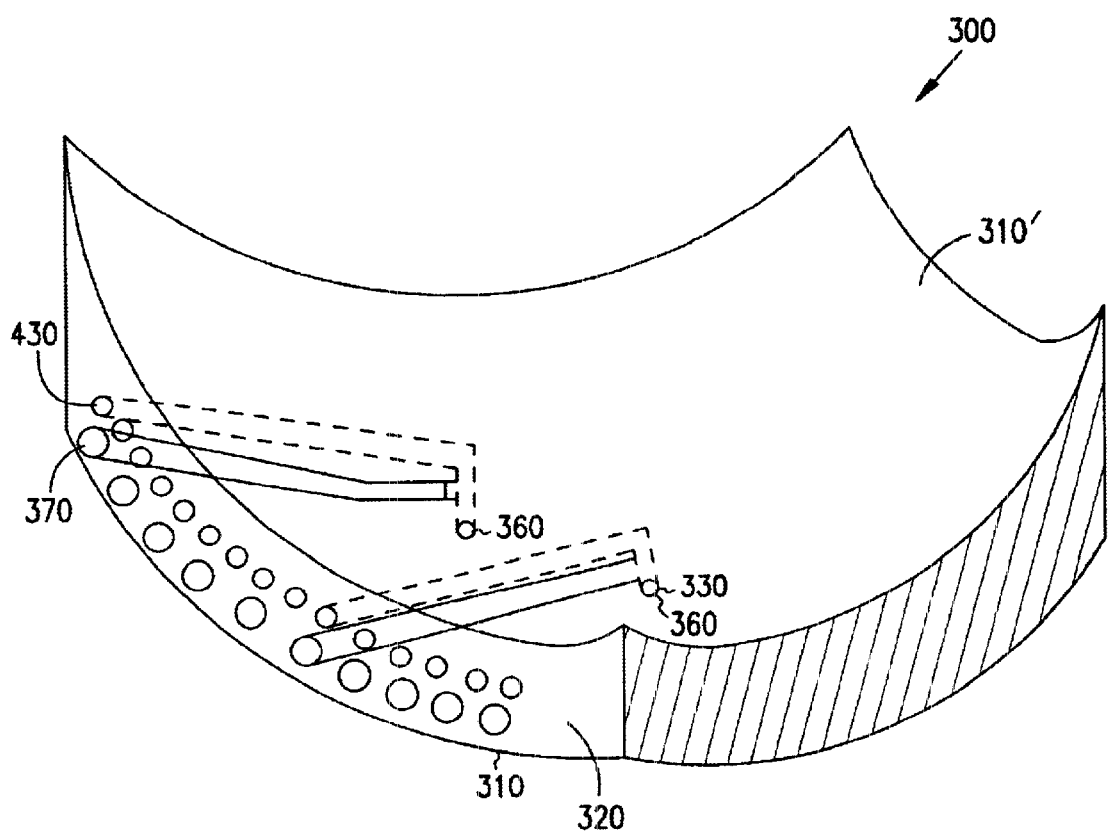
FIG. 4 is an isometric view of a first embodiment of a chip, which is a contoured implant, that has separate sites that is positioned near neurologic tissue.

FIG. 4 is an isometric view of a first embodiment of the chip 300 that shows several separate sites 360 that are adapted for positioning near neurologic tissue. In this particular embodiment, the chip 300 is curved so that it will fit the contour of the retina of the eye. It should be noted that this invention can be used in other applications other than the eye to selectively stimulate desired neurological cells. In FIG. 4, two sites 360 are shown or detailed. The remaining sites are not shown for the sake of clarity. It should be remembered, however, that there are a plurality of sites and for each particular site 360 there is at least one microfluidic channel 430 that includes an end 330 that opens to the major surface 310 of the chip 300. In addition, there is a light wave-guide or a fiber optic that is positioned within the chip and intersects the microfluidic channel 430. The geometry of the sites of neurotransmitter release may be catheter-like or needle-like to penetrate deeply into the tissue, or slightly raised to deliver uncaged drug to superficial layers.

As shown in FIG. 4, the microfluidic channel is essentially L-shaped. The microfluidic channel 430 terminates at the major surface 310 or opens to the major surface 310 forming a microfluidic channel or conduit end 330. At least a portion of the microfluidic channel or conduit 430 is transverse to the major surface 310 of the channel 300. The specific placement of the microfluidic channel may be varied. For example, as shown in FIG. 4 the microfluidic channel has an opening on the minor surface 320 of the chip 300.

Certain neurologic tissue is sensitive to light. For example, neurologic tissue associated with the retina or brain will be destroyed if light of a certain wavelength or light of a certain amount is received by that particular neurologic tissue. Therefore, as shown in FIG. 4, the light wave-guide 370 is essentially parallel to the major surface 310 of the chip 300. The microfluidic conduit or channel 430 crosses the light wave-guide in route to the major surface where it opens at a site 360. The light wave-guide 370 can carry light to the microfluidic channel to un-cage the molecules in the solution passing through the microfluidic channel or conduit 430 just before the solution passes onto the major surface 310 of the chip 300. Thus, the caged molecules in solution can be selectively un-caged by pulsing light through the light wave-guide 370. Further advantages that the light wave guide 370 is position parallel to the major surface 310, and as a result, the light passing through the wave guide 370 does not exit through the opening 330 of the microfluidic channel or conduit 430. The result is that light of most any type can be used to un-cage a molecule just before it passes to the major surface and the light will not be directed toward the sensitive neurologic tissue, such as neurologic tissue associated with the retina.

Figure 5:
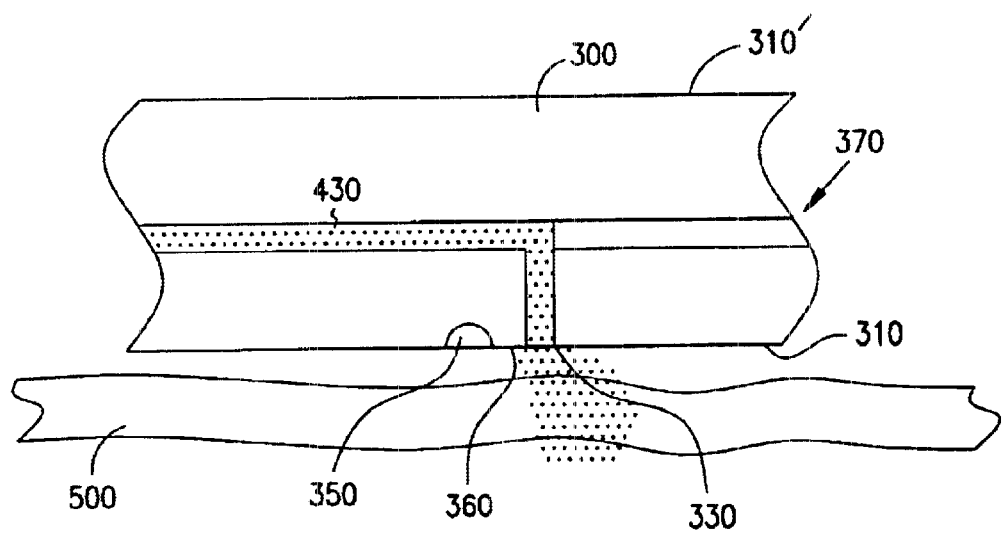
FIG. 5 is a diagram showing a cross section of one of the sites of the chip shown in FIG. 4.

FIG. 5 is a diagram showing a cross section of the chip 300 at one of the sites 360 as shown in FIGS. 3 and 4. The microfluidic channel 430 is L-shaped. The wave-guide 370 intersects the microfluidic channel 430 and remains essentially parallel to the first major surface 310 and the second major surface 310' of the chip 300. By passing light through the wave-guide 370 the previously caged molecules are un-caged and then passed to the first major surface 310 and exit the first major surface 310 at the opening of the conduit 330. The first major surface 310 includes the output ends of the conduits. The second major surface 310' does not have conduit ends in this particular embodiment. The un-caged molecules can then be delivered to the neurologic tissue 500. It should be noted that it takes approximately 1 micro Joule of light to un-cage a molecule. If the light were UV or ultraviolet light, this amount of light would destroy or substantially damage sensitive neurologic tissue 500 such as that associated with a retina 150. Light of various frequencies and wavelengths can be used to un-cage the molecules. In addition, the caged molecules are typically neurotransmitters such as glutamates, glycines, peptides, mimetic agents, a neuro-mimetic or a neurotransmitter-mimetic molecule or hormones. It is also possible to send down a solution that includes a plurality of caged molecules. For example, two caged neurotransmitters could be delivered in a solution to a particular site 360. In addition, the solution could include a neuro-protective agent that would protect the neuronal tissue. The solution could also include elements to selectively stimulate and antagonize portions of a cell. For example, the solution could be formulated to antagonize or achieve a center surround configuration of a stimulus point in space. The reason that neuro-protectors are needed is that certain drugs such as a glutamate sometimes trigger programmed cell degeneration. By adding a protective-agent, this degeneration can be essentially eliminated.

Figure 9:
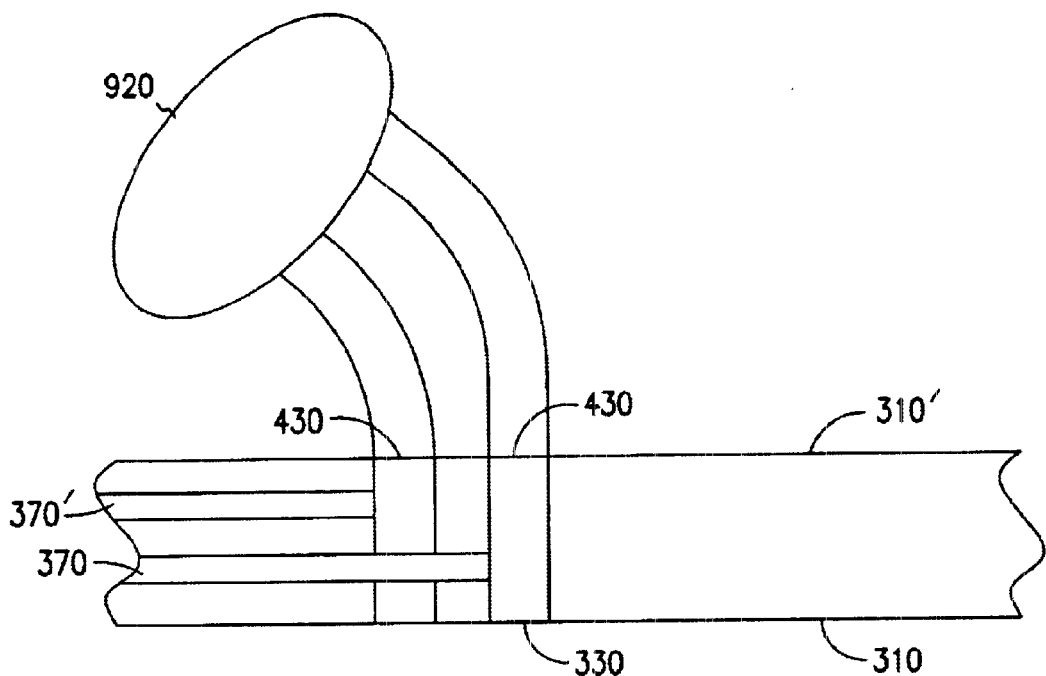
FIG. 9 is a cross section al view showing the microfluidic channel and wave guide of another embodiment of a chip, which is a contoured implant, for stimulation of neurological tissue.
Figure 10:
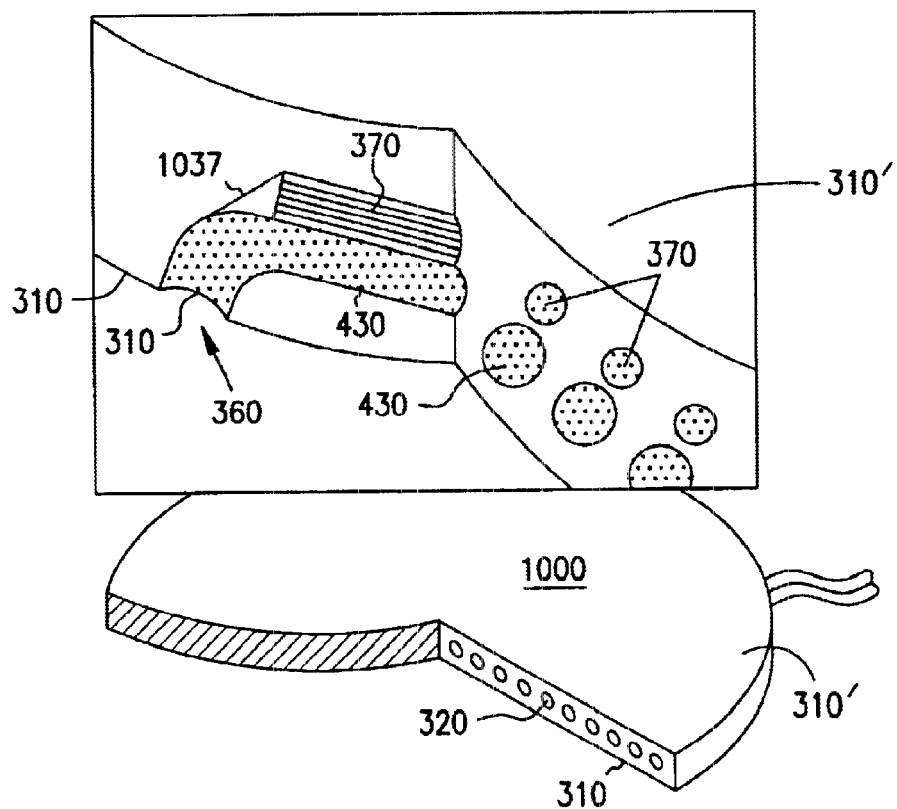
FIG. 10 is another cross sectional view of a chip, which is a contoured implant, for stimulation of neurological tissue.

In another embodiment shown in FIG. 9, the microfluidic channel 430 would go from one major surface 310' to the other major surface 310 of the chip 300. Fluid is delivered directly to major surface 310 but not directly to major surface 310'. The wave-guide or fiber optic cable 370, 370' for delivering light intersects the microfluidic channel 430 at a position remote from the major surface 310 of the chip 300.

As shown in FIG. 9, the light wave-guide 370 is essentially parallel to the major surface 310 of the chip 300. The microfluidic conduit or channel 430 crosses the light wave-guide in route to the major surface where it opens at a site 360. The light wave-guide 370 can carry light to the microfluidic channel to un-cage the molecules in the solution passing through the microfluidic channel or conduit 430 just before the solution passes onto the major surface 310 of the chip 300. Thus, the caged molecules in solution can be selectively un-caged by pulsing light through the light wave-guide 370. Further advantages that the light wave guide 370 is position parallel to the major surface 310, and as a result, the light passing through the wave guide 370 does not exit through the opening 330 of the microfluidic channel or conduit 430. The result is that light of most any type can be used to un-cage a molecule just before it passes to the major surface and the light will not be directed toward the sensitive neurologic tissue, such as neurologic tissue associated with the retina.

Each of the fluid channels 430 is attached to a fluid reservoir 920. The fluid reservoir may hold a fluid having several different caged molecules which can be uncaged using several different wavelengths of light. In this manner, a different wavelength of light may be passed down conduit 370' to open one type of caged molecular in solution and another wavelength of light is passed through wave guide 370 to open another type of caged molecule.

FIGS. 11 and 12 show yet another embodiment of a chip 1000. The chip 1000 includes a first major surface 310 and a second major surface 310'. The chip includes a plurality of microfluidic channels 430 which end or terminate at the major surface 310. The microfluidic channels terminate at the surface 310 with an end 330 of the conduit which opens onto the major surface 310 of the chip 1000. Sandwiched within the chip 1000 is a fiber optic cable or a plurality of fiber optic cables 370 for delivering light to the microfluidic channel 430. The wave guides or fiber optic cable 370 is cleaved at the end so that light passing through the channel reflects off the cleaved portion 1037 of the fiber optic or wave guide 370. The cleave is angled such that the light passing through the wave guide 370 will not pass back through the wave guide but will in fact be reflected toward the microfluidic channel 430 to which it is connected. Thus, light passing through the wave guide 370 can be used to uncage molecules in the fluid 430 in the microfluidic conduit before they passed to the major surface 310 where they are used for neurostimulation. Also advantageously, the light used will not be placed on the neurological cells and therefore the light will not damage these cells.

FIG. 12 shows the major surface of the chip 310 and then shows a cross section of a portion of that chip. The chip 1000 includes the microfluidic channel 430 and the wave guide 370 having an angled reflective end 1037. The reflective end 1037 is a cleaved end of the wave guide 370 which is cleaved at an angle so that all of the light pumped down the wave guide 370 is reflected and exits the wave guide at the intersection point with the microfluidic channel 430. The microfluidic channel 430 carries caged molecules. The microfluidic channel 430 can carry a single caged molecule or a plurality of caged molecules which are openable based upon the wave length of the light carried by the wave guide 370. Once the light is pulsed or passed through the wave guide 370, the light uncages the molecules in the fluid within the conduit 430 before they pass out of the end of the fluid conduit 330 and to the major surface 310 of the chip 1000. The major surface 310 of the chip 1000 is in contact with neurological tissue 500 containing neurological cells. The angled end or cleaved end of the wave guide 370, depicted by reference numeral 1037, prevents light from being directed onto the neurological tissue.

In operation the chip 300, 1000 is attached to the retina using a glue, tack or an adhesive. A transceral conduit allows a tube 130 for carrying the solution including caged molecules to the chip as well as the fiber optic cable 242 to pass into the eye and be connected to the chip 300. A seton draining implant 200 is also placed onto the eye so that excess fluid can drain from the major surface 310 of the chip 300, 1000 and out of the eye. The camera is used to produce an image. For example, the camera may be used to detect edges of an image. The computer 2000 produces a patterned light source. The patterned light source can be thought of as a frame of a television picture, for example. The frame has a certain amount of pixels representing varying intensities of light. Frame after frame are put together to form motion. Needless to say, a computer determines the pixels for each frame and outputs this as a patterned light source 220 to the link 230. The computer 2000 produces a series of frames and controls which pixels or which areas will be lit in the patterned light source 220 outputs from the computer according to certain software programs that may be modified according to the target organ to be stimulated. The patterned light source is then used to trigger the light source 240 associated with the second portion 232 of the link 230. The light source 240 then enables or sends down light to certain sites 360 on the chip 300. Light may travel down one wave-guide 370 and light may not travel down another wave-guide 370 so that molecules in solution will be un-caged at specific selected site 360 on the chip 300. In essence, the invention forms chemical pixels. Selected sites are provided with light down a conduit 370 so that molecules become un-caged at the specific sites where light has been provided. At the specific site where light has been provided, the un-caged molecules now are able to stimulate the neurologic cells at or near the site 370. Thus, in edge detection, for example, certain of the sites are provided with light un-caged to produce an outline of an object. Since chemical stimulation stimulates the center of the cell, the spatial relation can be maintained with greater accuracy.

Although it has been shown that the drug delivery system 100 could be used as a retinal implant, it is contemplated that the drug delivery system can be used to stimulate chemically all sorts of neurologic tissue. For example, neurologic tissue associated with the brain may be used to control movement disorders such as Parkinson's Disease. In addition the technique may be used to treat psychiatric disorders or hormonal deficiencies or psychological disorders. In addition, neurologic tissue associated with the spine might be able to control movement in a person's body. For example, a person with a severed spinal cord may be provided with the drug delivery system and inputs to the chip 300 could be used to control movement and trigger cell firing in neurologic tissue associated with the spinal cord. Other potential uses are for auditory prosthesis in the cochlea or auditory cortex. The drug delivery system can be used to deliver drugs to any neurologic tissue within a body or other tissue within the body. It should also be noted that only a portion of the caged molecules are un-caged to stimulate the neurologic tissue. In other words, only selected amounts of caged molecules are un-caged to stimulate cells at selected sites near the neurologic tissue to be stimulated.

Figure 6:
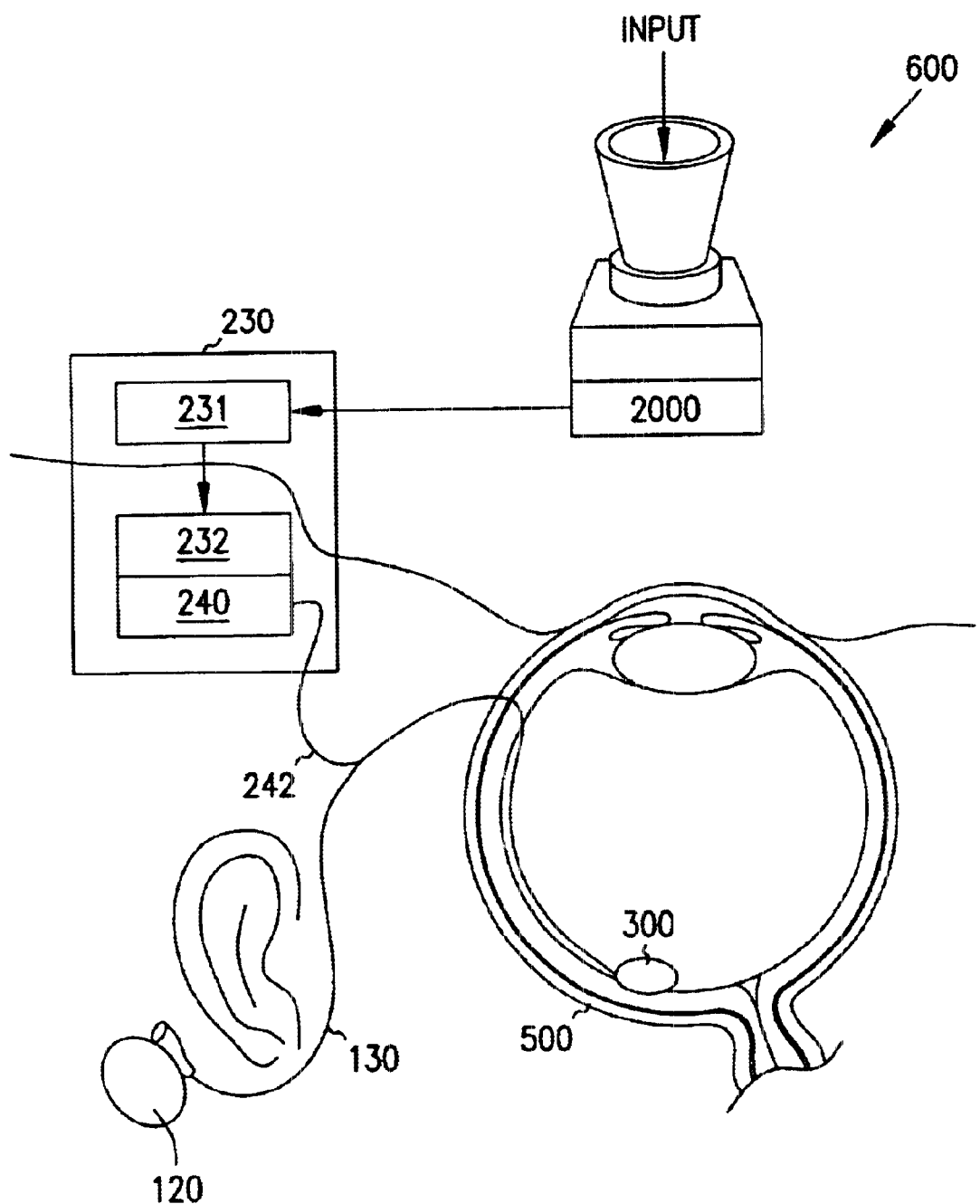
FIG. 6 is a schematic showing general use of the drug delivery system with any type of tissue, including neurologic tissue.

FIG. 6 is a schematic diagram showing general use of the drug delivery system 100. FIG. 6 is a generalized version of the drug delivery device 100. The drug delivery device 100 includes a computer 2000 that converts some inputs into an output that can be placed upon a grid. In essence, the output is a patterned light source that is input to a first portion 231 of the link 230. The link 231 passes the information to the second portion 232 of the link 230. In this particular instance, the second portion 232 of the link is positioned within a body 600. The link 232 includes a light source 240 that takes the patterned light source output and actually turns it into or converts it to light that is passed down the fiber optic cable 242 to the chip 300. There is also a source of caged molecules that may include neurotransmitters and neuro-protectors. The reservoir of the solution may include one or more of these neurotransmitters or protectors-protectors. The solution is pumped using a pump 120 through a tube 130 to the chip 300. Texas Instruments Corporation has a digital light processor that is a micro mirror device. Ultraviolet light can be directly shown upon this chip and it will turn off various pixels that you want on or off to produce a patterned stimulus. The Texas Instrument digital light processor could be used as the light source 240 within the body 600. The chip 300 includes a plurality of sites that can be selectively turned on and off by the computer controlled light source 240. Certain of the sites 360 (shown in FIG. 3) can be provided with un-caged molecules while at certain other sites the caged molecules are not un-caged. This produces chemical stimulation at various selected sites 360 (as shown in FIG. 3). This selected pattern of stimulation can then be used to stimulate any type of neural tissue or any type of tissue 500. For example, neural tissue associated with the brain or the spinal cord could be selectively stimulated as well as neural tissue associated with an auditory function.

Figure 7:
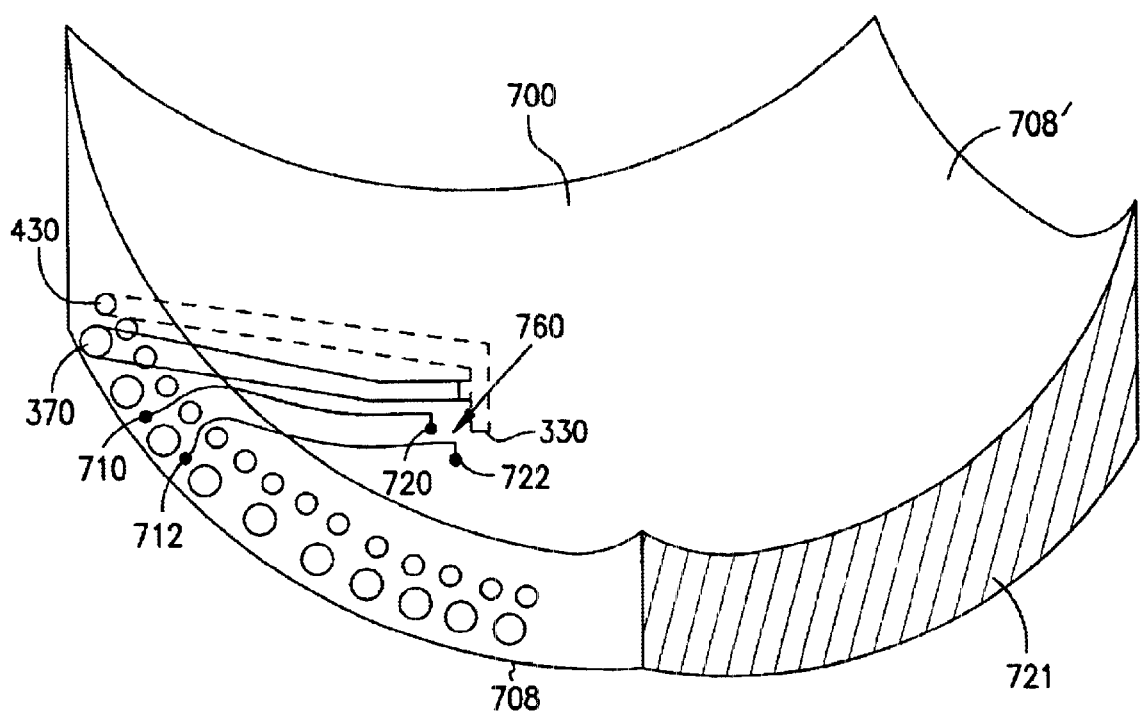
FIG. 7 is an isometric view of a second embodiment of a chip, which is a contoured implant, that has separate sites that is positioned near neurologic tissue.

FIG. 7 is an isomeric view of another embodiment of a chip 700 that has separate sites that are adopted to be positioned near neurologic tissue 500 within a body 600. The chip 700 includes a first major surface 708, a second major surface 708', and a minor surface 721. The chip includes a microfluidic channel or conduit 430 as well as a light wave-guide 370. The chip also includes a plurality of sites 760. For the sake of clarity, only one of the sites 760 is shown. Light is provided along the wave guide 370 to the intersecting microfluidic channel 430 to selectively un-cage molecules and provide a chemical stimulus to tissue 500 that may be adjacent or near the opening 330 of the microfluidic channel. The chip 700 also includes electrical traces 710 and 712. The electrical traces have paths located on the chip at the major surface 708 associated with a site 760. The first major surface 708 includes the plurality of sites 760. The second major surface 708' is devoid of sites 760. In other words, this particular chip 700 is a hybrid and includes both chemical stimulation by selectively un-caging molecules that pass through the microfluidic channel 430 and electrical stimulation. The chip can also produce electrical stimulation at the paths 720 and 722 on the major surface 708 of the chip 700. In some instances, it may be advantageous to stimulate using electrical energy and in other instances it may be advantageous to stimulate using a chemical neurotransmitter that has been un-caged. In other instances, it may be appropriate or advantageous to provide both. In some embodiments for some applications, the uncaged molecule is iontophoretically driven into the tissue by utilizing an electrical current. The role for electrodes is either to electrically stimulate the tissue with an electrical current to pass a low level current to provide an iontophoretic electromotive force to drive the uncaged molecule into the target tissue.

Figure 8:
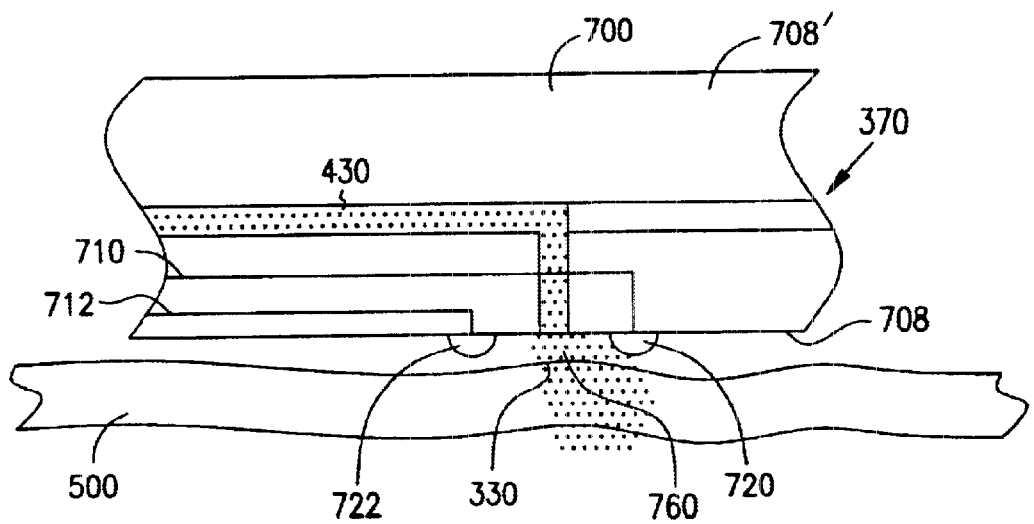
FIG. 8 is a diagram showing a cross section of one of the sites of the chip shown in FIG. 7.

FIG. 8 shows a cross section of one of the sites 760 of the chip 700 shown in FIG. 7. As shown in FIG. 8, the wave-guide 370 intersects the microfluidic channel or conduit 430 so that caged molecules passing through the conduit can be selectively un-caged to provide chemical stimulation of tissue 500 positioned near the site 760 of the chip 700. In addition, the chip includes electrical traces 710 and 712 that have electrodes 722 and 720 presented at the site 760 for electrical stimulation of the neurologic tissue 500. In this particular instance, the computer 2000 controls both the un-caging of molecules as well as the electrical stimulus at the electrode 720 and 722.

Figure 13:
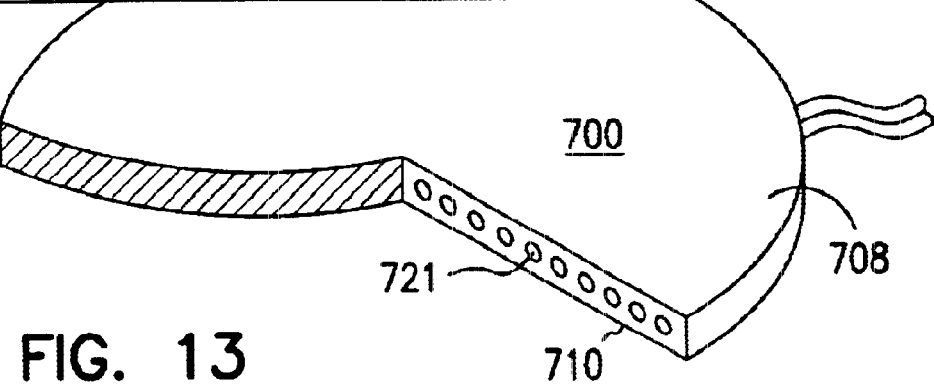
FIG. 13 is a cut away isometric view of another embodiment of the chip, which is a contoured implant, for stimulation of neurological tissue.

FIG. 13 is an isometric view of still another embodiment of a chip 700 that has separate sites that are adapted to be positioned near neurologic tissue 500 within a body 600. The chip 700 includes a major surface 708 and a minor surface 721. The chip includes a microfluidic channel or conduit 430 as well as a light wave-guide 370. The wave guide terminates at an angle 1037 so that the light passed through the wave guide is reflected toward the microfluidic channel 430. The chip also includes a plurality of sites 760. For the sake of clarity, only one of the sites 760 is shown. Light is provided along the wave guide 370 to the intersecting microfluidic channel 430 to selectively un-cage molecules and provide a chemical stimulus to tissue 500 that may be adjacent or near the opening 330 of the microfluidic channel. The chip 700 also includes electrical traces 710 and 712. The electrical traces have paths located on the chip at the major surface 708 associated with a site 760. In other words, this particular chip 700 is a hybrid and includes both chemical stimulation by selectively un-caging molecules that pass through the microfluidic channel 430 and electrical stimulation. The chip can also produce electrical stimulation at the paths 720 and 722 on the major surface 708 of the chip 700. The first major surface 708 includes elements for un-caging molecules. The second major surface 708' does not have elements for un-caging molecules. In some instances, it may be advantageous to stimulate using electrical energy and in other instances it may be advantageous to stimulate using a chemical neurotransmitter that has been un-caged. In other instances, it may be appropriate or advantageous to provide both. In some embodiments for some applications, the uncaged molecule is iontophoretically driven into the tissue by utilizing an electrical current.

Figure 14:
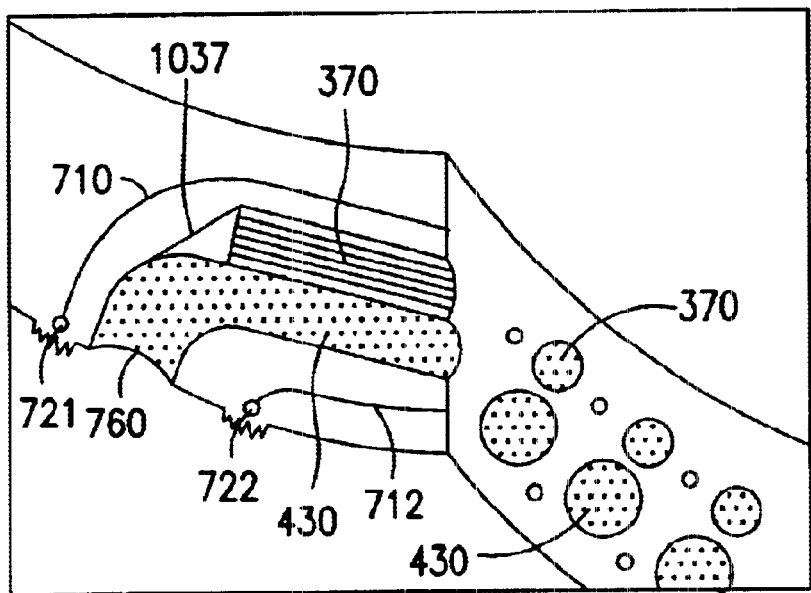
FIG. 14 is a cross sectional view of the chip shown in FIG. 13.

FIG. 14 shows a cross section of one of the sites 760 of the chip 700 shown in FIG. 13. As shown in FIG. 14, the wave-guide 370 intersects the microfluidic channel or conduit 430 so that caged molecules passing through the conduit can be selectively un-caged to provide chemical stimulation of tissue 500 positioned near the site 760 of the chip 700. The wave guide terminates at an angle 1037 so that the light passed through the wave guide is reflected toward the microfluidic channel 430. In addition, the chip includes electrical traces 710 and 712 that have electrodes 722 and 720 presented at the site 760 for electrical stimulation of the neurologic tissue 500. In this particular instance, the computer 2000 controls both the un-caging of molecules as well as the electrical stimulus at the electrode 720 and 722.

The invention is not limited to having one microfluidic channel or conduit per site 360. The invention contemplates having a plurality of microfluidic channels per site 360. In addition, the invention also contemplates having more than one wave-guide 370 per site 360. With more than one wave-guide 370 per site 360, light of various wavelengths could be transmitted to a microfluidic conduit or conduits to selectively un-cage molecules.

Figure 15:
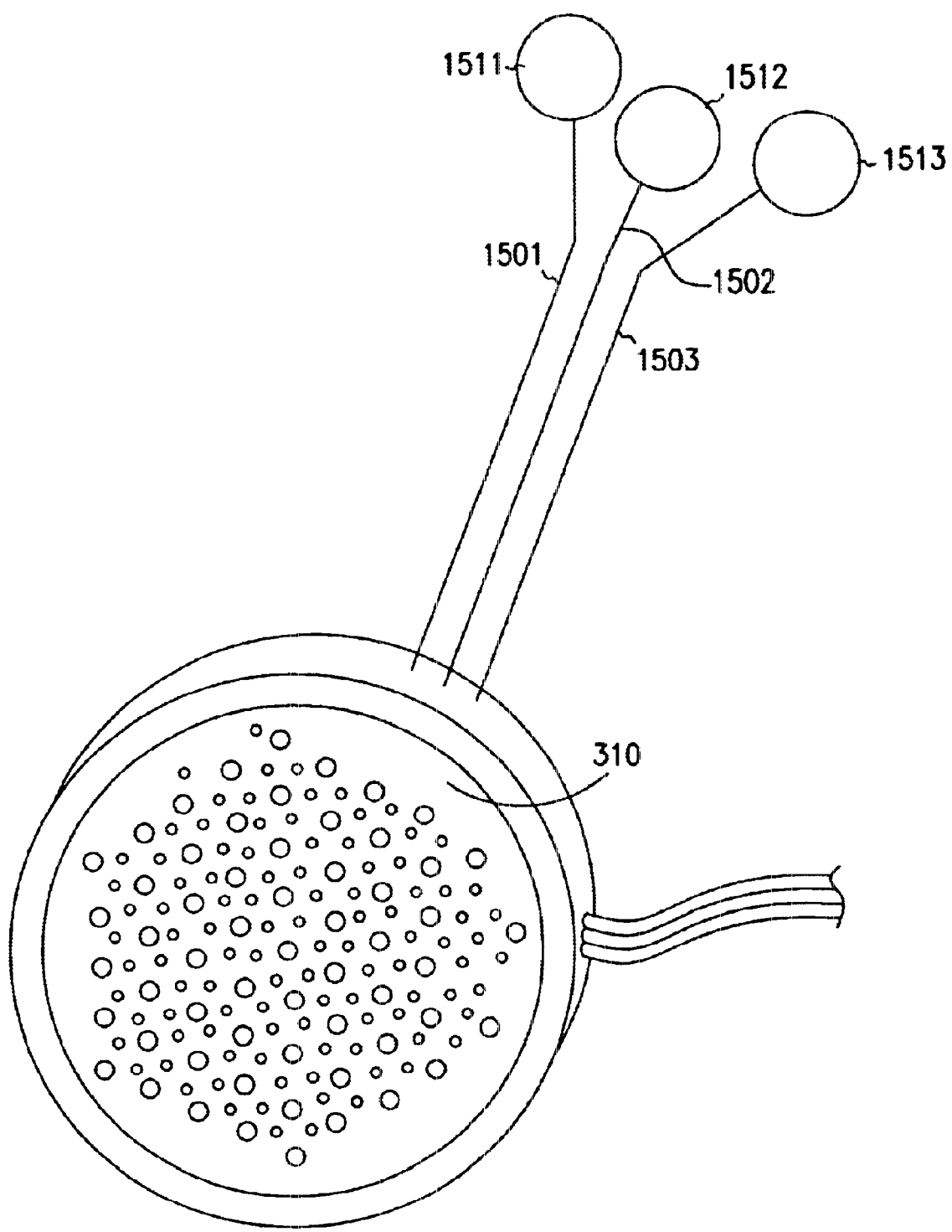
FIG. 15 is a schematic of a drug delivery system having multiple fluid reservoirs.

In another embodiment shown schematically in FIG. 15, the fluid channel includes a plurality of separate fluid channels 1501, 1502, 1503 which are attached to several different pumps and several different fluid reservoirs 1511, 1512, 1513. Several microfluidic channels may be grouped and attached to a first pump and reservoir and one or more other microfluidic channels may be attached to a second pump and reservoir. Each of the microfluidic channels may conduct a unique caged-molecular compound or compounds. Each microfluidic channel will have its own, unique optical path for photolytic activation. In this way, agonist and antagonist molecules could be delivered in a spatially and temporally controlled manner using similar or dissimilar wavelengths of light. In other words, in one embodiment a plurality of microfluidic channels, contains subsets of microfluidic channels. Each subset of microfluidic channels serves as a conduit for a particular fluid. For example, the subsets of microfluidic channels could each carry one or more caged molecules so that a plurality of caged neurotransmitter substances can be delivered to the chip at different sites 360 on the chip. The groups of microfluidic channels may end or terminate at the major surface 310 of the chip in selected shapes, such as a plurality of concentric circles or other shapes as are formed by groups of microfluidic channels.

It should be noted that in addition to caged molecules other chemical formulations for neurostimulation of tissue are contemplated and may be used. For example, it is contemplated that a chemical which changes shape in the presence of light may also be used to stimulate neurological tissue. In other words, a molecule would have a first conformation or shape when not in the presence of light from the wave guide. This would be in an inactive conformation or shape and would not stimulate the neurological tissue near the major surface where the fluid conduit interact with the neurological tissue 500. In the presence of light passing down the wave guide, the molecule could have another active conformation or another shape which would serve to stimulate the neurological tissue near the end of the microfluidic conduit 330. The advantage of such a system is that uncaging a molecule requires the cleavage of bonds. When cleaving the bonds of the caged molecules, large amounts of energy are required and therefore UV or ultra violet light, which has the appropriate amount of energy to cleave bonds, must be used. It is contemplated that using a molecule which changes shape or which has an active confirmation and an inactive confirmation would be much more efficient and therefore high energy light would not have to be passed down through the wave guide 370. This would be a much more efficient neurostimulation system. The molecules that would change confirmation to render it active could be merely photoactivated or photoactivatable. In other words, photoactivated drugs could be activated either photolytically or otherwise. Photolysis generally requires a high energy light source such as ultraviolet where the molecule servicing as a cage must be cleaved or chemical bonds must be broken which can only be done with ultraviolet light. Using a molecule which changes confirmation between an active and inactive state is a much more efficient way of achieving a desired goal of neurotransmitter stimulation. In other words, a lot lower energy level of light can be used to photoactivate the molecules to a state where they have an active confirmation.

Figure 16:
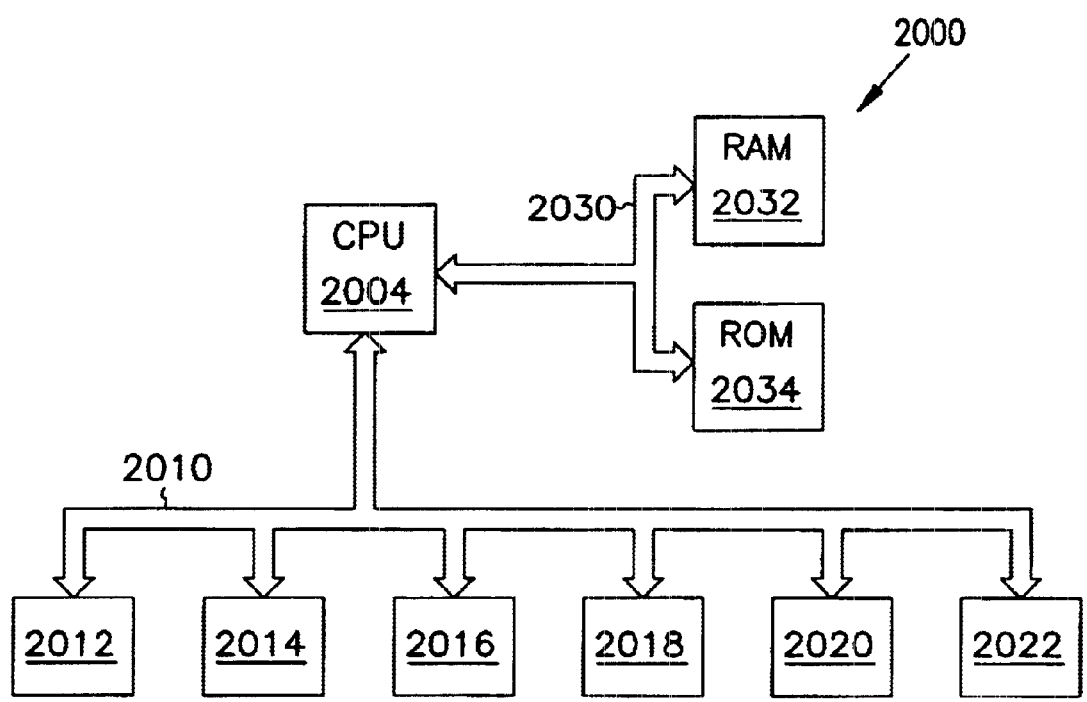
FIG. 16 is a schematic view of a computer system.

FIG. 16 is a schematic view of a computer system. Advantageously, the invention is well suited for use in a computer system 2000. The computer system 2000 may also be called an electronic system or an information handling system and includes a central processing unit, a memory and a system bus. The information handling system includes a central processing unit 2004, a random access memory 2032, and a system bus 2030 for communicatively coupling the central processing unit 2004 and the random access memory 2032. The information handling system 2000 includes a disc drive device that includes the ramp described above. The information handling system 2000 may also include an input/output bus 2010 and several devices peripheral devices, such as 2012, 2014, 2016, 2018, 2020, and 2022 may be attached to the input output bus 2010. Peripheral devices may include hard disc drives, magneto optical drives, floppy disc drives, monitors, keyboards and other such peripherals.

Advantageously, the method and apparatus stimulates cells at the cell center (soma or dendrites) to precisely stimulate certain cells. This method and apparatus stimulates the neural tissue and produces a predictable perception when spatial relation is needed. A further advantage is that the resulting implantable device is biocompatible and remains biocompatible.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A drug delivery system comprising:
   a device having a plurality of sites;
   a fluid channel for delivering a drug to one of the plurality of sites associated with the device;
   a light channel associated with the device, the light channel for delivering light to the fluid channel while preventing delivery of light directly to one of the plurality of sites.

2. The drug delivery system of claim 1 wherein the fluid channel is a micro fluidic channel.

3. The drug delivery system of claim 1 wherein the light channel is a wave guide.

4. The drug delivery system of claim 1 wherein the light channel is a fiber optic cable.

5. The drug delivery system of claim 1 wherein the light channel includes a fiber optic cable and a wave guide.

6. A drug delivery system comprising:
a chip having a plurality of sites;
a fluid channel associated with the chip for delivering a drug to one of the plurality of sites; and
a light channel associated with the chip for delivering light to an area near one of the plurality of sites, wherein at least a portion of the drug delivery system is housed on a chip.

7. The drug delivery system of claim 6 wherein the light channel intersects the fluid channel.

8. The drug delivery system of claim 6 wherein the chip further comprises:
a first major surface;
a second major surface; and
a minor surface, wherein the sites are on one of the first major surface or the second major surface, the fluid channel adapted to deliver fluid to a site on one of the first major surface or the second major surface and wherein the light channel directs light at the fluid channel wherein light from the light channel does not substantially exit to the first major surface or the second major surface.

9. A drug delivery system comprising:
a chip further comprising:
a first major surface;
a second major surface;
a plurality of sites associated with one of the first major surface or the second major surface;
a fluid channel for delivering a drug to one of the plurality of sites;
a light source;
a light channel for delivering light from the light source to an area near one of the plurality of sites; and
a pump in fluid communication with at least one of the plurality of sites.

10. The drug delivery system of claim 9 further comprising a digital light processor;
the digital light processor receiving an input and outputting light in response to the input.

11. The drug delivery system of claim 10 wherein the input to the digital light processor is an RF signal.

12. The drug delivery system of claim 10 wherein the digital light processor is adapted for subcutaneous use.

13. The drug delivery system of claim 9 further comprising electrodes positioned near a site.

14. A chip comprising:
a first major surface;
a second major surface;
a minor surface;
a duct in fluid communication with the first major surface; and
a wave guide, adapted to transmit light, which intersects the duct, wherein light transmitted by the wave guide does not substantially exit to the first major surface.

15. The chip of claim 14 further comprising an electrode positioned near the duct at the first major surface.

16. The chip of claim 14 wherein the wave guide terminates at an angle with respect to the duct.

17. A drug delivery system comprising:
a plurality of sites on a surface of a device;
a plurality of fluid channels associated with the device for delivering a drug to the plurality sites, wherein at least one of the fluid channels is in fluid communication with each of the plurality of sites;
a plurality of light guides associated with the device operatively coupled with each of the plurality of fluid channels, the plurality of light guides delivering light directly to the fluid channel without delivering light directly to the plurality of sites.

18. The drug delivery system of claim 17 wherein the plurality of fluid channels are micro fluidic channels.

19. The drug delivery system of claim 17 wherein the plurality of light guides are wave guides.

20. The drug delivery system of claim 17 wherein the plurality of light guides are fiber optic cables.

21. The drug delivery system of claim 17 wherein the plurality of light guides include a fiber optic cable portion and a wave guide portion.

22. A drug delivery system comprising:
a substrate including a plurality of sites;
a plurality of fluid channels associated with the substrate for delivering a drug to the plurality sites, wherein at least one of the fluid channels is in fluid communication with each of the plurality of sites;
a plurality of light guides associated with the substrate operatively coupled with each of the plurality of fluid channels, wherein the plurality of sites are located on a chip.

23. A drug delivery system comprising:
a plurality of sites on a substrate;
a plurality of fluid channels associated with the substrate for delivering a drug to the plurality sites, wherein at least one of the fluid channels is in fluid communication with each of the plurality of sites; and
a plurality of light guides associated with the substrate operatively coupled with each of the plurality of fluid channels, wherein the plurality of sites are located on a chip having
a first major surface; and
a second major surface wherein the fluid channels output fluid at the first major surface, wherein the light guides intersect the plurality of fluid channels, wherein light from the light guide does not substantially exit to the first major surface.

24. The drug delivery system of claim 23 further comprising a link adapted to be positioned within a body, said light channels being attached to an optical link.

25. The drug delivery system of claim 23 further comprising a trans-cutaneous optical link adapted to be positioned on a surface of a body.

26. The drug delivery system of claim 23 further comprising an RF link adapted to be positioned within a body.

27. The drug delivery system of claim 23 further comprising:
a camera;
a computer operatively coupled to the camera, the computer converting a video input from the camera to an output; and
a link for receiving the computer output and converting the output to a series of light pulses for passing through selected ones of the plurality of light guides at selected times.

28. A drug delivery device comprising:

means for delivery of a solution of a photoactivatable neuro-active drug to a preselected area in vivo; and a device for photo activating said photoactivatable neuro-active drug in said solution proximate said preselected area, the device for photo activating said photoactivatable neuro-active drug not directing light to the preselected area.

29. A drug delivery device comprising:

means for delivery of a plurality of units of solution of a photoactivatable neuro-active drug to a plurality of preselected areas in vivo; and means for photo activating at least a portion of the plurality of units of said drug near at least a portion of said preselected areas in vivo, but not directing light to the preselected areas in vivo.

30. The drug delivery device of claim 29 wherein the neuro-active drug could be an antagonist or agonist of neuronal activity.

31. The drug delivery device of claim 29 wherein the neuro-active drug could be an antagonist or agonist of neuronal activity.

32. A method for delivering drugs comprising:

providing a solution including caged molecules;

delivering caged molecules to a position near a site;

selectively uncaging a selected portion of the caged molecules at a position near the site; and delivering the uncaged molecules to the site.

33. A drug delivery device comprising:

a substrate further comprising
   a plurality of sites;

a plurality of fluid channels for delivering a drug to one of the plurality sites;

a light channel for delivering light to an area near one of the plurality of sites;

a first reservoir in fluid communication with a first subset of the plurality of fluid channels; and a second reservoir in fluid communication with a first subset of the plurality of fluid channels.

34. The drug delivery device of claim 33 made of biocompatible material and adapted to be positioned proximate neurological tissue.

35. The drug delivery device of claim 33 wherein the first fluid reservoir includes a first photoactivable neuro-active drug and wherein the second fluid reservoir includes a second photoactivable neuro-active drug.

36. The drug delivery device of claim 33 wherein the first subset of the plurality of fluid channels form a pattern at the plurality of sites.

37. The drug delivery device of claim 33 wherein the first subset of the plurality of fluid channels form a pattern at the plurality of sites and wherein the second subset of the plurality of fluid channels form a pattern at the plurality of sites;

for delivery of a plurality of units of solution of a photoactivatable neuro-active drug to a plurality of preselected areas in vivo; and means for photolytically activating at least a portion of the units of said drug at least a portion of said preselected areas.

* * * * *